US005468263A

United States Patent [19]

Chung et al.

[11] Patent Number: 5,468,263
[45] Date of Patent: Nov. 21, 1995

[54] FUEL COMPOSITION CONTAINING ALKYLPHENYL POLY(OXYALKYLENE) POLYAMINE ACID ESTER

[75] Inventors: Hyun-jong Chung; Sang-chul Yim, both of Seoul; Bon-chul Ku, Kyoungsangnam-do; Ho-young Guen, Kyoungsangnam-do; Duk-han Kim, Kyoungsangnam-do, all of Rep. of Korea

[73] Assignee: Yukong Limited, Seoul, Rep. of Korea

[21] Appl. No.: 201,165

[22] Filed: Feb. 18, 1994

[30] Foreign Application Priority Data

Feb. 19, 1993 [KR] Rep. of Korea .................. 93-2298

[51] Int. Cl.⁶ ........................................ C10L 1/18
[52] U.S. Cl. ..................... 44/39 L; 44/410; 560/169; 560/193; 560/198
[58] Field of Search ............................. 560/169, 193, 560/198; 44/391, 410

[56] References Cited

U.S. PATENT DOCUMENTS 2,761,874  9/1956  Bersworth et al. ............. 560/169
3,979,442  7/1976  Schafer et al. ................. 560/169
4,075,411  2/1978  Dickstein ....................... 560/224
4,321,062  3/1982  Herbstman et al. ............. 44/391
4,326,069  4/1982  Stockinger et al. ............. 560/169

*Primary Examiner*—Prince Willis, Jr.
*Assistant Examiner*—Cephia D. Toomer
*Attorney, Agent, or Firm*—Abelman, Frayne & Schwab

[57] ABSTRACT

The present invention relates to an alkylphenyl poly(oxyalkylene) polyamine acid ester fuel detergent effective for controlling deposit generated in an automobile engine, prepared by reacting polyamine and alkylphenyl poly(oxyalkylene) maleate derivative prepared by reaction of alkylphenyl poly(oxyalkylene) alcohol and maleic anhydride, through Michael reaction. A fuel detergent diluted solution comprising 5–70 wt % of said fuel detergent and an inert organic solvent, and a hydrocarbon fuel composition comprising thereof are prepared. The present invention does not use deadly toxic phosgene gas used in preparation of a deposit control additive for conventional polyether amine deposit control additive and prevents generation of amine salt to eliminate the process for removing amine salt. The present invention does not use excessive polyamine, minimizing the consuming amount of the polyamine and eliminates the process for removing and recovering the polyamine salt such that it provides a new fuel detergent showing excellent detergency.

8 Claims, No Drawings

FUEL COMPOSITION CONTAINING ALKYLPHENYL POLY(OXYALKYLENE) POLYAMINE ACID ESTER

FIELD OF THE INVENTION

The present invention relates to an alkylphenyl poly(oxyalkylene) polyamine acid ester compound of general formula (V) for preventing generation of deposits or removing deposits generated in an automobile engine. More particularly, the present invention relates to a compound for deterging fuel (hereinafter, fuel detergent), fuel detergent diluted solution comprising said fuel detergent, a process for preparing said fuel detergent and a fuel composition comprising said fuel detergent showing improvements in a driving efficiency and fuel economy, and reducing exhaust gas by removing the entire deposit existing in, intake systems of an automobile engine.

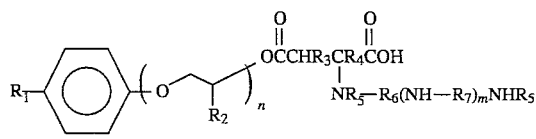

Wherein, $R_1$ is straight chained or branched alkyl group containing from 4 to 25 carbon atoms, $R_2$ and $R_5$ are H or alkyl group containing from 1 to 3 carbon atoms, independently, $R_3$ and $R_4$ are H or alkyl group containing from 1 to 3 carbon atoms, independently, $R_6$ and $R_7$ are alkylene group containing from 2 to 6 carbon atoms, n is an integer which makes the molecular weight of the compound to be 400 to 4,000 and m is 0 or an integer between 1–5.

BACKGROUND OF THE INVENTION

Deposits on many inner parts of the engine are generally resulted by incomplete combustion of hydrocarbon fuel used for automobile engine. Deposits in the engine degrade the efficiency of the engine. One of these problems is that the resultant hydrocarbon deposit is deposited in combustion chamber, thereby decreasing space in the combustion chamber on compressing the mixture of fuel and air such that a compression ratio is which is higher than the designed one, causing a heavy knocking. Furthermore, continued knocking for a long term causes fatigue stress or abrasion in major parts of the engine. A fuel with high octane number can be used to reduce engine knocking to solve one of these problems but the fuel with high octane number is expensive. The carbon deposit around carburetor prevents air flow on idling or a low speed driving to make a fuel-air mixture containing excessive amount of fuel. These conditions result in incomplete combustion of fuel to make engine idling rough and induce exhausting of excessive amount of hydrocarbon and carbon monoxide.

U.S. Pat. No. 4,881,945 discloses that alkylphenyl poly(oxyalkylene) amino carbamate as polyether amine is effective for controlling the amount of fuel deposit. A desired fuel detergent is obtained by reacting alkylphenyl poly(oxyalkylene) alcohol with phosgene to a chloroformate intermediate, followed by reacting it with polyamine in the above U.S. patent. In the meantime, the phosgene gas is not easy to handle industrially because of its deadly toxicity and a complex process is required to remove unreacted phosgene gas and resultant hydrogen chloride gas.

U.S. Pat. Nos. 4,881,945, 4,160,648, 4,243,798, 4,191,537 and 4,197,409 disclose that 15 equivalent polyamine to chloroformate are used to make monoaminocarbamate and the excessive polyamine should be removed by washing it with distilled water after reaction. In this case, excessive amount of polyamine is used such that it is wasted a lot and should be recovered accompanying an onerous and uneconomic process. Polyamine hydrochloride is obtained in a same ratio with desired aminocarbamate by reaction of polyamine and chloroformate intermediate but the resultant chloride salt is not only bad for a fuel but also causing corrosion and plugging of the apparatus such that it should be maintained in a low level.

SUMMARY OF THE INVENTION

An object of the present invention is to provide an alkylphenyl poly(oxyalkylene) polyamine acid ester compound of the above formula (V) through alkylphenyl poly(oxyalkylene) maleate as an intermediate, in order to eliminate the process for removing unreacted phosgene gas and hydrogen chloride generated in preparation of chloroformate, an intermediate, in the above prior arts, to simplify the process by adding polyamine through Michael reaction, and to make the mass production easily by removing side effects occurred by resultant salt.

Another object of the present invention is to provide a fuel detergent diluted solution comprising the alkylphenyl poly(oxyalkylene) polyamine acid ester compound for a fuel detergent and the other object of the present invention is to provide a hydrocarbon fuel composition comprising an alkylphenyl poly(oxyalkylene) polyamine acid ester compound or fuel detergent diluted solution.

The other object of the present invention is to provide a process for preparing the compound of formula (V). The other object of the present invention is to provide an intermediate, alkylphenyl poly(oxyalkylene) maleate derivative of the formula (I) for preparing the fuel detergent and a process for preparing thereof.

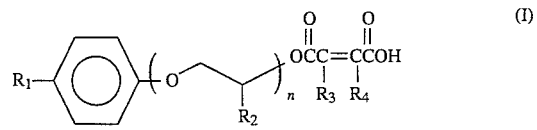

Wherein, $R_1$, $R_2$, $R_3$ and $R_4$ are the same as stated in formula (V), and n is an integer which makes molecular weight of the compound of the formula (I) to be 400–3,700.

DESCRIPTION OF THE PREFERRED EMBODIMENTS

The present invention is comprised of a new alkylphenyl poly(oxyalkylene) polyamine acid ester compound of the formula (V) for a fuel detergent,

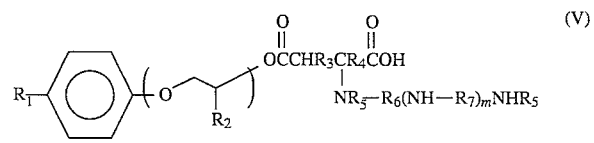

wherein, $R_1$ is straight chained or branched alkyl group containing from 4 to 25 carbon atoms, $R_2$ and $R_5$ are H or alkyl group containing from 1 to 3 carbon atoms, independently, $R_3$ and $R_4$ are H or alkyl group containing from 1 to 3 carbon atoms, independently, $R_6$ and $R_7$ are alkylene group containing from 2 to 6 carbon atoms, n is an integer which makes the molecular weight of the compound to be 400 to 4,000 and m is 0 or an integer between 1–5.

The new fuel detergent with alkylphenyl poly(oxyalkylene) polyamine acid ester compound of the formula (V) in accordance with the present invention has an average molecular weight of about 400–4,000, and preferably about 1,000–3,000.

The compound of formula (V) is prepared by reaction of alkylphenyl poly(oxyalkylene) maleate derivative of formula (I) prepared by the reaction of alkyl-alkyleneoxide monol of formula (II) and maleate derivative of formula (III) or maleate derivative anhydride of formula (III)-1, and polyamine of formula (IV). More particularly, the fuel detergent comprising the reaction product of alkylphenyl poly(oxyalkylene) maleate and polyamine, which has an excellent detergency, is prepared by polymerizing alkylene oxide containing at least more than 2 carbon atoms, such as ethylene oxide, propylene oxide, or butylene oxide, with alkyl phenol to obtain alkylphenyl poly(oxyalkylene) alcohol, reacting alkylphenyl poly(oxy-alkylene) alcohol with maleate derivative or anhydrides thereof in the presence of a catalyst or in its absence to obtain alkylphenyl poly(oxyalkylene) maleate derivative and then reacting the derivative with a polyamine of formula (IV).

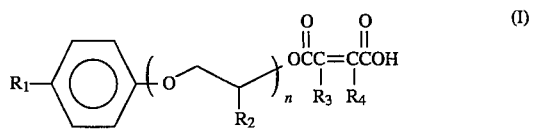

wherein, $R_1$, $R_2$, $R_3$ and $R_4$ are the same as stated in formula (V), and n is an integer which makes molecular weight of the compound of the formula (I) to be 400–3,700.

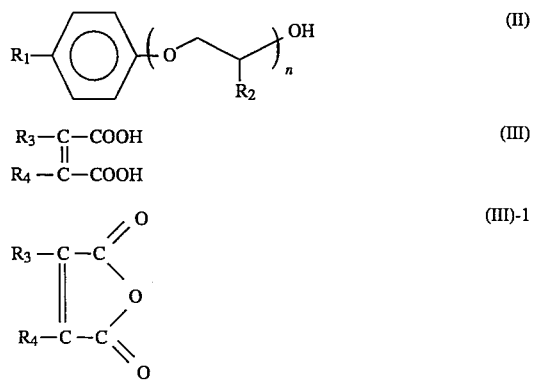

wherein, $R_1$, $R_2$, $R_3$ and $R_4$ are the same as stated in formula (V), and n is an integer which makes molecular weight of the compound of the formula (II) to be 400–3,600.

$$R_5\text{—HN—}R_6\text{—(—NH—}R_7\text{—)m—NH—}R_5 \quad \text{(IV)}$$

wherein, $R_5$, $R_6$, $R_7$ and m are the same as stated in formula (V).

The present invention is comprised of alkylphenyl poly(oxyalkylene) maleate derivative of said formula (I), an intermediate of end product of the invention having formula (V) to achieve another object of the invention. The intermediate is also a new compound which is included in the present invention.

The alkylphenyl poly(oxyalkylene) maleate derivative of formula (I), connecting alkylphenyl poly(oxyalkylene) alcohol useful for preparing a fuel detergent of alkylphenyl poly(oxyalkylene) polyamine acid ester compound having formula (V), with polyamine, is obtained by reacting alkylphenyl poly(oxyalkylene) alcohol with maleate derivative or anhydride thereof with the equivalent ratio of 1:1 to 1:5, more preferably the ratio of 1:1 to 1:2 in an inert solvent at a temperature of 10°–200° C., more preferably 60°–140° C., for 1 to 20 hours, more preferably 1 to 10 hours with stirring at a certain speed in the presence of catalyst or without it.

Said inert solvent is an inactivated aromatic or aliphatic organic solvent and the useful hydrocarbon solvent is hexane, cyclohexane, Isopa G, benzene, toluene, xylene or mixture thereof, and more preferably xylene. The catalyst in the present invention is strong acid catalyst, Lewis catalyst or basic catalyst, such as triethylamine, p-toluene sulfonic acid, dibutyltin oxide and titanium isoperoxide, and triethylamine is used as to maleic anhydride with the equivalent ratio of 0.01–1, and more preferably 0.1–0.5.

The useful connecting group is maleic anhydride, 2,3-dimethyl maleic anhydride, 2-methyl maleic anhydride, 2-ethyl maleic anhydride, maleic acid, 2,3-dimethyl maleic acid, 2-methyl maleic acid, or 2-ethyl maleic acid, and more preferably maleic anhydride.

The preferred polyamine, being represented by the formula (IV), is alkylene diamine or polyalkylene polyamine as well as substituted polyamine and hereinafter designated as polyamine.

A more preferred polyamine is polyamine having 2 to 12 nitrogen atoms and 4 to 26 carbon atoms or alkylene polyamine having 2 to 3 hydrocarbon, and more specifically lower alkylene polyamine such as ethylene diamine, diethylene triamine, triethylene tetramine, tetraethylene pentamine, propylene diamine and propylene triamine.

The fuel detergent of alkylphenyl poly(oxyalkylene) polyamine acid ester in accordance with the present invention is preferably one having at least one primary or secondary nitrogen atom in the molecular structure, and more preferably lower alkylene polyamine having at least more than 2 nitrogen atom.

On preparing the final product of the present invention, as various substitution isomers can exist in those instances that each nitrogen in polyamine is not identical geometrically, the isomers are included in the final product of the present invention. The mixtures including dimer compounds, being a by-product of the present invention, are also included in the final product of the invention.

The process for preparing an alkylphenyl poly(oxyalkylene) polyamine acid ester compound, being another object of the present invention, comprises the reaction of alkylphenyl poly(oxyalkylene) maleate derivative of the formula (I) and polyamine of the formula (IV) in the equivalent ratio of 0.5:1 to 1:20, more preferably in the equivalent ratio of 1:1 to 1:2 at a temperature of 5°–150° C., more preferably 20°–90° C. for 1 to 20 hours, more preferably 1 to 5 hours.

The fuel diluted solution having a fuel detergent of the formula (V) to accomplish the another object of the invention is comprised of an inert organic solvent with boiling point of 100° to 200° C. and a fuel detergent of the formula (V) with 5 to 70 wt. %, more preferably 30 to 50 wt. %. The preferred organic solvent is benzene, toluene, xylene or an aromatic solvent having a higher boiling point than them, and most preferably aromatic organic solvent of Kocosol 100 (a mixed aromatic solvent, Yukong Limited, Korea).

The fuel detergent of the present invention is generally used for hydrocarbon fuel having a boiling point of gasoline or diesel fuel, such as volatile oil or light oil. The amount of the fuel detergent added to the fuel diluted solution depends on the kind of the fuel, and the kind and amount of the additives in the fuel. It is preferable to use the fuel detergent in an amount of 50 to 5,000 ppm, more preferably 100 to 1,000 ppm and clean-up property of removing deposit in intakes can be expected in case of more than 2,000 to 5,000 ppm. Additionally, antioxidants, antiknocking agents, or MTBE(Methyl Tert-Butyl Ether) may be present in the fuel having the present detergent.

The fuel detergent and the process for preparing thereof, the fuel detergent diluted solution comprising said detergent and their properties and effects in accordance with the present invention are illustrated in detail in the following examples. However, the present invention is not limited by the following examples.

EXAMPLE 1

Preparation of tetrapropenylphenyl poly(oxybutylene) alcohol 52.4 g of tetrapropenylphenol was dissolved in 50 ml of toluene and the solution was put into a high-pressure reactor equipped with a temperature controller and a stirrer. 1.56 g of potassium was cut into a tiny form and heated to 60° C. to dissolve the potassium. It was cooled to 40° C. and under nitrogen atmosphere, 331 g of butylene oxide was slowly added using a injection pump for 30 minutes to 1 hour. After addition, the high-pressure reactor was heated to 110° C. gradually. The pressure of the reactor was raised up to 4 atm on proceeding the reaction for 4 hours under stirring. When the pressure of the reactor went back to atmosphere, the reaction was accomplished. The reactor was cooled to 60° C. and 20 g of Magnesol (magnesium silicate) and 200 mg of Filteraid were stirred for 20 minutes and then filtered using a filter funnel to obtain a mixture dissolved in toluene. Toluene was removed under reduced pressure to obtain tetrapropenylphenyl poly(oxybutylene) alcohol as sticky and light yellowish liquid. The mean molecular weight and OH value of the product were 1,600 and 34.5, respectively and it showed characteristic peaks at 3,400 $cm^{-1}$ and 1,108 $cm^{-1}$ by FT-IR.

EXAMPLE 2

Preparation of tetrapropenylphenyl poly(oxypropylene) alcohol 52.4 g of tetrapropenylphenol was dissolved in 50 ml of toluene and the solution was put into a high-pressure reactor equipped with a temperature controller and a stirrer. 1.56 g of potassium was cut into a tiny form and heated to 60° C. to dissolve the potassium. It was cooled to 30° C. and under nitrogen atmosphere, 290 g of propylene oxide was added gradually using a injection pump for 30 minutes to 1 hour. After addition, the high-pressure reactor was heated to 90° C. gradually. The pressure of the reactor was raised up to 7 arm on proceeding the reaction for 10 hours with stirring. When the pressure of the reactor went back to atmosphere, the reaction was accomplished. The reactor was cooled to 60° C. and 20 g of Magnesol and 200 mg of Filteraid were stirred for 20 minutes and then filtered using a filter funnel to obtain a mixture dissolved in toluene. Toluene was removed under reduced pressure to obtain tetrapropenylphenyl poly(oxypropylene) alcohol as sticky and light yellowish liquid. The mean molecular weight and OH value of the product were 1,500 and 37.5, respectively and it showed characteristic peaks at 3,400 $cm^{-1}$ and 1,100 $cm^{-1}$ by FT-IR.

EXAMPLE 3

Preparation of tetrapropenylphenyl poly(oxybutylene) maleate 48 g of tetrapropenylphenyl poly(oxybutylene) alcohol (mean molecular weight =1,600) according to the example 1 was dissolved in 50 ml of xylene and the solution was put into a 3 connected round bottom flask of 250 ml, equipped with a thermometer, a condenser and a dropping funnel. 3 g of maleic anhydride was put and dissolved with stirring at a room temperature. After being dissolved completely, the reaction solution was heated to 80° C. and after 2 ml of triethylamine was diluted into 10 times with xylene, it was injected gradually using a injection pump for 1 hour. The reactor was kept to proceed the reaction at 90° C. for 3 hours. Once, it was ascertained that the reaction was completed by (Thin Layer Chromatography), the reactor was cooled. Unreacted maleic anhydride and triethylamine were washed with 100 ml of distilled water. The reaction mixture dissolved in xylene was obtained. Magnesium sulfate was added to remove water and a filter funnel was used for filtering to obtain a clean yellowish mixture solution. The solvent in filtrate was removed to obtain 46 g of liquid product. The product showed characteristic peak at 1,730 $cm^{-1}$ by FT-IR.

EXAMPLE 4

Preparation of tetrapropenylphenyl poly(oxypropylene) maleate 45 g of tetrapropenylphenyl poly(oxypropylene) alcohol (mean molecular weight =1,500) according to the example 2 was dissolved in 50 ml of xylene and the solution was put into a 3 connected round bottom flask of 250 ml, equipped with a thermometer, a condenser and a dropping funnel. 3 g of maleic anhydride was put and dissolved under stirring at room temperature. After being dissolved completely, the reaction solution was heated to 80° C. and after 2 ml of triethylamine was diluted into 10 times with xylene, it was injected gradually using a injection pump for 1 hour. The reactor was kept to proceed the reaction at 90° C. for 3 hours. Once, it was ascertained that the reaction was completed by TLC, the reactor was cooled. Unreacted maleic anhydride and triethylamine were washed with 100 ml of distilled water. The reaction mixture dissolved in xylene was obtained. Magnesium sulfate was added to remove water and a filter funnel was used for filtering. The solvent in filtrate was removed to obtain 4 g of a viscous and yellowish liquid product. The product showed characteristic peak at 1,730 $cm^{-1}$ by FT-IR.

EXAMPLE 5

Preparation of tetrapropenylphenyl poly(oxybutylene) ethylene diamine acid ester 46 g of tetrapropenylphenyl poly(oxybutylene) maleate according to the example 3 was dissolved in 50 ml of xylene and the solution was put into a 3 connected round bottom flask of 250 ml, equipped with a thermometer, a condenser and a dropping funnel. 1.8 g of ethylene diamine dissolved in 10 ml of toluene was put into the reactor using a dropping funnel. After the ethylene diamine was put into the reactor, the reaction was proceeded for 2 hours at a room temperature. Once, it was ascertained that the reaction was completed by TLC, the resultant was diluted with n-hexane and moved to a separatory funnel. The diluted solution was washed with 50 ml of distilled water to remove unreacted polyamine and by-products.

The water in the organic layer was removed with magnesium sulfate. After obtaining the resultant dissolved in the organic solvent by filtering, 46 g of product was obtained by removing the organic solvent under the reduced pressure. The preparation of the product was identified by characteristic peaks at 1,731 cm$^{-1}$ and 1,607 cm$^{-1}$ on FT-IR. The mean molecular weight of the product identified by GPC was 1,740. The content of nitrogen atom in the product was 1.27 wt %.

EXAMPLE 6

Preparation of tetrapropenylphenyl poly(oxypropylene) ethylene diamine acid ester 46 g of tetrapropenylphenyl poly(oxypropylene) maleate according to the example 4 was dissolved in 50 ml of xylene and the solution was put into a 3 connected round bottom flask of 250 ml, equipped with a thermometer, a condenser and dropping funnel. 1.8 g of ethylene diamine dissolved in 10 ml of toluene was put into the reactor using a dropping funnel. After the ethylene diamine was put into the reactor, the reaction was proceeded for 3 hours at a room temperature. Once, it was ascertained that the reaction was completed by TLC, the resultant was diluted with n-hexane and moved to a separatory funnel. The diluted solution was washed with 50 ml of distilled water to remove unreacted polyamine and by-products.

The water in the organic layer was removed with magnesium sulfate. After obtaining the resultant dissolved in the organic solvent by filtering, 46 g of product was obtained by removing the organic solvent under the reduced pressure. The preparation of the product was identified by characteristic peaks at 1,731 cm$^{-1}$ and 1,606 cm$^{-1}$ on FT-IR. The mean molecular weight of the product identified by GPC was 1,630. The content of nitrogen atom in the product was 1.38 wt %.

EXAMPLE 7

Preparation of a fuel detergent diluted solution containing tetrapropenylphenyl poly(oxybutylene) ethylene diamine acid ester.

The fuel detergent diluted solution (A) was prepared with 70–30 wt % of Kocosol-100(Yukong Limited, Korea), and tetrapropenylphenyl poly(oxybutylene) ethylene diamine acid ester prepared by the example 5 and the viscosity at 40° C. is reported in the following table 1.

EXAMPLE 8

Preparation of a fuel detergent diluted solution containing tetrapropenylphenyl poly(oxypropylene) ethylene diamine acid ester.

The fuel detergent diluted solution (B) was prepared with 70–30 wt % of Kocosol-100 (Yukong Limited, Korea), and tetrapropenylphenyl poly(oxypropylene) ethylene diamine acid ester prepared by the example 6 and the viscosity at 40° C. is reported in the following table 1.

TABLE 1

| Sample No. | A (wt. %) | B (wt. %) | Viscosity (cst) |
|---|---|---|---|
| 1 | 30 | 70 | 5.4 |
| 2 | 50 | 50 | 7.5 |
| 3 | 70 | 30 | 13.8 |
| 4 | 70 | 30 | 4.9 |
| 5 | 70 | 50 | 6.8 |
| 6 | 50 | 70 | 13.2 |

Note)
A is prepared with tetrapropenylphenyl poly(oxybutylene) ethylene diamine acid ester of example 5 and
B is prepared with tetrapropenylphenyl poly(oxypropylene) ethylene diamine acid ester of example 6.

Note) A is prepared with tetrapropenylphenyl poly(oxybutylene) ethylene diamine acid ester of example 5 and B is prepared with tetrapropenylphenyl poly(oxypropylene) ethylene diamine acid ester of example 6.

EXAMPLE 9

Detergency test in engine intake valve

A detergency test in engine intake valve was carried out with a fuel composition containing the fuel detergent diluted solution prepared with the example 7. The engine was a 1.6L DOHC engine, Elantra manufactured by Hyundae Automobiles Co. Ltd., Korea in 1991 and the characteristics were as follows.

Engine Type: DOHC type with 4 engine cylinders
Max. Output: 126/6000(PS/rpm)
Bore X Stroke: 82.3×75 mm
Max. Torque: 15.3/5000(kg/rpm)
Displacement: 1596 cc
Fuel Supply Type: MPI
Compression Ratio: 9.2
Max. Speed: 180 km/hr The test mode was Benz M102E and the test conditions were as follows.

Duration: 60 hrs
Torque: 3.1–3.7 Nm
Oil Tem.: 95°–100° C.
RPM: 800–3000
Cooling Water Tem.: 90°–95° C.
Cycle: 4.5 min. (Repeating 800)
Gear Changing: 1596 cc
Air Inlet Tem.: 35°±2° C.

The amount of the deposit generated in the intake valve was measured 0.1 mg unit by taking a part of the intake valve after disassembling the engine, washing with hexane and then drying it.

After the test, the valve was disassembled to remove the deposit at the bottom of the valve. The valve was washed until the washed water got to be clear. The valve washed was dried in an oven and then weight difference of the valve after and before the test was determined as an amount of the deposit.

The amount of deposit in a fuel without additive and that in a fuel with conventional additive was determined, varying the amount of the fuel diluted solution with 200 ppm and 400 ppm.

TABLE 2

|  | Amount of Deposit (mg) | |
| --- | --- | --- |
| Fuel without Additive | 180 | |
|  | 200 ppm | 400 ppm |
| Fuel with Sample No. 1 | 39.1 | 24.1 |
| Fuel with Sample No. 5 | 58.5 | 37.2 |

The table 2 shows that in the fuel having 200 ppm and 400 ppm of a fuel detergent diluted solution containing tetrapropenylphenyl poly(oxybutylene) ethylene diamine acid ester according to the example 7, 39.1 mg and 24.1 mg of deposit was deposited in the intake valve, respectively. There is a decreasing effect of 78% and 86% compared with the fuel which does not contain a detergent, forming 180 mg of deposit.

The fuel having tetrapropenylphenyl poly(oxypropylene) ethylene diamine acid ester of example 8 showed a decreasing effect of 67% and 79% whereas showing lower detergency compared with the fuel having tetrapropenylphenyl poly(oxybutylene) ethylene diamine acid ester of example 7.

What we claim is:

1. An alkyphenyl poly(oxyalkylene) polyamine acid ester compound of formula (V) for a fuel detergent, comprising at least one primary or secondary nitrogen atom and a repeating unit of alkylene oxide with at least more than 2 carbon atoms,

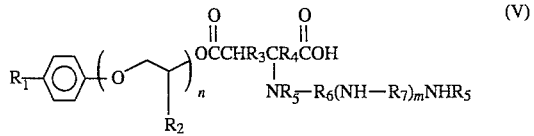

wherein, $R_1$ is straight chained or branched alkyl group containing from 4 to 25 carbon atoms, $R_2$ is an alkyl group containing from 1 to 3 carbon atoms and $R_5$ is H or an alkyl group containing from 1 to 3 carbon atoms, independently, $R_3$ and $R_4$ are H or alkyl groups containing from 1 to 3 carbon atoms, independently, $R_6$ and $R_7$ are alkylene groups containing from 2 to 6 carbon atoms n is an integer which makes the molecular weight of the compound to be 400 to 4000 and m is 0 or an integer between 1 and 5.

2. A diluted detergent solution comprising 5 to 70 wt % of the fuel detergent of formula (V) according to claim 1 and an inert organic solvent.

3. The diluted fuel detergent solution according to claim 2, comprising 30 to 50 wt % of said fuel detergent.

4. The diluted fuel detergent solution according to claim 2, wherein said inert organic solvent is an aromatic or aliphatic organic solvent having a boiling point of 100 to 200° C.

5. A hydrocarbon fuel composition comprising the compound of formula (V) according to claim 1 and a liquid hydrocarbon fuel.

6. The composition according to claim 5 comprising about 50 to 5,000 ppm of said compound of formula (V).

7. The composition according to claim 5, wherein said hydrocarbon fuel has a boiling point of gasoline or diesel fuel.

8. A hydrocarbon fuel composition comprising the diluted fuel detergent solution according to claim 2 and a liquid hydrocarbon fuel.

* * * * *